United States Patent [19]
Laudon et al.

[11] Patent Number: 5,500,225
[45] Date of Patent: Mar. 19, 1996

[54] METHOD FOR DETERMINATION OF URINE COMPONENTS AND FOR PREVENTING SUDDEN INFANT DEATH SYNDROME

[75] Inventors: Moshe Laudon, Kfar Saba; Nava Zisapel, Tel Aviv, both of Israel

[73] Assignee: Neurim Pharmaceuticals (1991) Ltd., Tel Aviv, Israel

[21] Appl. No.: 139,404

[22] Filed: Oct. 19, 1993

Related U.S. Application Data

[63] Continuation-in-part of Ser. No. 697,714, May 9, 1991, abandoned.

[51] Int. Cl.$^6$ .................................................. A61K 9/20
[52] U.S. Cl. ........................ 424/464; 424/467; 424/482
[58] Field of Search ........................ 424/464; 514/455, 514/634

[56] References Cited

U.S. PATENT DOCUMENTS

| | | | |
|---|---|---|---|
| 4,600,723 | 7/1986 | Short et al. | 514/416 |
| 4,654,361 | 3/1987 | Samples et al. | 514/419 |
| 4,855,325 | 8/1989 | Naftchi | 514/634 |
| 4,945,103 | 7/1990 | Cohen | 514/419 |
| 5,023,270 | 6/1991 | Goupil | 514/455 |
| 5,151,446 | 9/1992 | Horn | 514/617 |

FOREIGN PATENT DOCUMENTS

| | | |
|---|---|---|
| 0330652 | 8/1989 | European Pat. Off. |
| 8807370 | 10/1988 | WIPO |
| 8904659 | 6/1989 | WIPO |

OTHER PUBLICATIONS

Sparks, et al., *Journal of Pineal Research*, 5:111–118 (1988).
Sparks et al., Sudden Infant Death Syndrome (SIDS) and the Third Eye–II, Abstract No. 127, 5th Coll. Eur. Pineal Study Group, Guilford, U.K., Sep. 2, 1990.
Wurtman et al., Human Pineal Function in Physiologic States and Diseases, Abstract No. 024, 5th Coll. Eur. Pineal Study Group, Guilford, U.K., Sep. 2, 1990.
Wurtman et al., Melatonin in Humans: Possible Involvment in SIDS, and Use in Contraceptives, *Advances in Pineal Research* 5:319–327 (1991).
Sturner et al., Melatonin Concentrations in the Sudden Infant Death Syndrome, *Forensic–Sci–Int.* 45:171–80 (1990) (Medline Abstract).
Weissbluth et al., Sudden Infant Death Syndrome: A Genetically Determined Impaired Maturation of the Photoneuroendocrine System. A Unifying Hypothesis, *J. Theor. Biol.* 167:13–25 (1994) (Medline Abstract).
Laudon et al., Neuroendocrinology, 48,577, 1988.

*Primary Examiner*—Thurman K. Page
*Assistant Examiner*—William E. Benston, Jr.
*Attorney, Agent, or Firm*—Rothwell, Figg, Ernst & Kurz

[57] ABSTRACT

Non-volatile organic components of interest in the urine of humans using diapers are assayed by carrying out the following sequence of steps at least once and up to as many times as the diapers are changed in a given 24-hour period, namely: removing the outer cover and any extraneous material from a used diaper so as to leave only diaper pulp with absorbed urine, estimating the amount of water in the used diaper, extracting a weighed portion of the diaper pulp with a water-miscible organic solvent, in which the diaper pulp is insoluble, to give an extract containing a component of interest, and determining the amount of the component of interest per unit volume of urine absorbed on the diaper pulp by analyzing an aliquot of the extract. The method may be applied e.g. to the prevention of sudden infant death syndrome in infants, by selecting infants for medication with melatonin where diaper urine indicates a deficiency of its metabolite 6-sulfatoxymelatonin in a 24-hour period. The melatonin may be administered in the form of a pharmaceutical formulation, or in an infant food which is included within the invention.

18 Claims, 1 Drawing Sheet

METHOD FOR DETERMINATION OF URINE COMPONENTS AND FOR PREVENTING SUDDEN INFANT DEATH SYNDROME

The present application is a continuation-in-part application from U.S. application Ser. No. 07/697,714, filed May 9, 1991, now abandoned in the name of Nava Zisapel, one of the inventors of the present invention, and entitled "Method for Correcting Plasma Melatonin Levels and Pharmaceutical Formulation Comprising Melatonin".

FIELD AND BACKGROUND OF THE INVENTION

The present invention relates to a method for determination of components of urine in diapers, as well as to a method for preventing sudden infant death syndrome (i.e. cot death), which makes use of the results of such determination.

In one aspect, this prior patent application (U.S. Ser. No. 07/697,714) relates to a pharmaceutical controlled-release formulation, which comprises melatonin in combination with at least one pharmaceutical carrier, diluent or coating, which formulation releases melatonin into the plasma following administration to a human patient, according to a profile which simulates that of the normal human endogenous melatonin profile depicted in FIG. 1 of that patent application.

In another aspect, the prior patent application (U.S. Ser. No. 07/697,714) relates to a method for correcting a melatonin deficiency or distortion in the plasma melatonin level and profile in a human subject, which comprises administering to a human in which such a deficiency or distortion had been diagnosed, over a time period including at least part of the nocturnal period, an effective plasma melatonin deficiency or distortion correcting amount of melatonin in the form of a pharmaceutical controlled-release formulation defined in the preceding paragraph.

In yet another aspect, the prior patent application (U.S. Ser. No. 07/697,714) relates to a method for the prevention of sudden infant death syndrome in infants, which comprises the steps of:

(a) screening at least one infant in order to determine the plasma melatonin level(s) thereof;

(b) selecting at least one infant shown in step (a) to have a deficient plasma melatonin level; and (c) administering an effective plasma melatonin deficiency correcting amount of melatonin to the at least one selected infant from step (b), the melatonin being in the form of a pharmaceutical controlled-release formulation defined above.

The entire contents of U.S. application Ser. No. 07/697,714 are incorporated herein by reference.

U.S. Pat. No. 4,600,723 discloses the administration of melatonin in order to alleviate or prevent the negative effects of disturbances in circadian rhythms of bodily performance and function, such as may occur in a change of work patterns from day to night shift, or in cases of jet lag. Although conventional oral administration is exemplified, there is mentioned the possibility of administering melatonin a slow release form to maintain high plasma levels for the whole sleep period.

U.S. Pat. No. 4,654,361 discloses the administration of melatonin order to lower intraocular pressure in a human, where such pressure is abnormally high. Conventional oral and topical routes of administration are mentioned.

U.S. Pat. No. 4,945,103 discloses a method of treating premenstrual syndrome by administering melatonin at dosage levels sufficient to alleviate the symptoms. The melatonin may be administered orally or parenterally, or in the form of an implant or suppository which will provide a sustained release of melatonin over time.

PCT Patent Application No. WO 88/07370 discloses the administration of melatonin for the purpose of inhibiting ovulation in human females, thereby effecting contraception, as well as for preventing breast cancer in women. The melatonin may be administered orally or parenterally, or in the form of an implant providing a sustained release of melatonin over time.

PCT Patent Application No. WO 89/04659 discloses the use of melatonin or related compounds, as a component in pharmaceutical compositions in order to counteract the effects of aging.

European Patent Application No. 0330625A2 discloses the production of melatonin and analogs thereof, as well as the use of melatonin administered orally, intramuscularly or endovenously for various therapeutic purposes.

The entire contents of U.S. Pat. No. 4,600,723, U.S. Pat. No. 4,654,361, U.S. Pat. No. 4,945,103, PCT Patent Application No. WO 88/07370, PCT Patent Application No. WO 89/04659 and European Patent Application No. 0330625A2, and of the U.S. issued patent equivalents, to the extent that these exist, of WO 88/07370, WO 89/04659 and EP 0330625A2, are explicitly incorporated herein by reference.

It may be noted that sudden infant death syndrome (SIDS) or cot death is a phenomenon in which an apparently healthy infant of 1–12 months of age dies suddenly, usually duping sleep. It has been shown that while body and brain weight of age-matched control and SIDS infants were not significantly different, the size of the pineal gland was significantly reduced in SIDS infants ($p<0.000$; Sparks and Hunsaker, J. Pin. Res. 5:111 (1988), and Abstract No. 127 of the 5th Colloquium of the European Pineal Study Group, Guildford, U.K., Sep. 2, 1990). Additionally, melatonin levels in the SIDS infant blood were lower by about 50% in SIDS compared with control infants ($p<0.05$; Wurtman and Lynch, Abstract No. 24 of the 5th Colloquium of the European Pineal Study Group, Guildford, U.K., Sep. 2, 1990). If, as seems likely from these reports, melatonin serves a critical Pole in sleep functions of the human infant, administration of melatonin to infants with a deficient melatonin level (according to the method of U.S. application Ser. No. 07/697,714, or otherwise) could prevent SIDS.

It is evidently essential to be able to readily screen infants in the age group susceptible to SIDS, in order to determine their plasma melatonin levels, and to select infants for treatment with melatonin, in order to prevent SIDS, as far as possible.

More generally, determination of urine components is often desired for diagnostic purposes. These components may be, for example, hormones and metabolites such as corticosteroids, creatinine, uric acid and catecholamines. Assays based on urine have several advantages over plasma assays, and in particular: (a) sample collection is non-invasive, (b) frequent sample collection is readily achieved, (c) hormones and metabolites accumulate in urine and thus information is not lost if some time points in a sequence have been omitted, and (d) biosafety—whereas patients' specimens and kit calibration components should be handled as if capable of transmitting infections such as hepatitis B or AIDS, these risks are lower in urine samples compared with plasma samples.

For most purposes, urine samples are collected once, usually in the morning, or accumulated for 24 hours in a reservoir, and samples of the total daily excretion are assessed. Plasma levels of most hormones, and consequently urinary levels of these hormones, and/or their metabolites, show regular diurnal fluctuations (circadian rhythms). To diagnose rhythm disturbances, these hormones need to be assessed in the blood or urine, at regular intervals over the 24 hour period, including during the night.

In infants (and in disabled or bedridden patients who do not control urine excretion), urine collection is complicated and is done by attachment to the urethral outlet of specially designed baskets. These devices are cumbersome and often become detached. Frequent sampling for assessment of circadian rhythm disturbances is almost impossible in such cases.

A very useful approach to facilitate chronobiological type diagnosis in infants (or in disabled or bedridden patients) would be to determine hormone or metabolite content in the diapers. However, such a method is limited by practical problems. A major drawback is associated with the fact that disposable diapers can absorb urine very efficiently (about 200 times their weight), but the urine cannot be recovered from the diapers, even by centrifugation. To extract materials from diapers, one needs to soak them with large volumes of water, which is not a suitable technique for mass diagnostic routines.

SUMMARY OF THE INVENTION

In accordance with the present invention, a method has been discovered for recovering urinary components from the diapers. This method facilitates urinary measurements in infants in general and in particular enables chronobiological diagnosis to be performed.

Thus, the present invention provides in one aspect a method for the determination of non-volatile organic components of interest in the urine of human subjects using diapers, which comprises carrying out the following sequence of steps at least once and up to as many times as the diapers are changed in a given 24-hour period, namely: providing a diaper which has been used to absorb urine from a human subject, removing the outer cover and any extraneous material so as to leave substantially only diaper pulp having urine absorbed thereon, estimating the amount of water in the used diaper, extracting a weighed portion of the diaper pulp having urine absorbed thereon with a water-miscible organic solvent, in which the diaper pulp is insoluble, to give an extract containing a component of interest, and determining the amount of the component of interest per unit volume of urine which was absorbed on the diaper pulp by assaying an aliquot of the extract.

The water-miscible organic solvent may comprise e.g. at least one member selected from water-miscible alcohols, water-miscible acids, water-miscible bases, acetone, acetonitrile, dimethylsulfoxide and water-miscible amides. The presently preferred solvent is selected from methanol and ethanol.

The component of interest may be e.g. selected from hormones and metabolites, e.g. corticosteroids, creatinine, uric acid or catecholamines. A particular component of interest is 6-sulfatoxymelatonin.

In another aspect, the invention provides a method for the prevention of sudden infant death syndrome in infants, which comprises the steps of: (a) screening one or more infants in order to determine the plasma melatonin level(s) thereof; (b) selecting infant(s) shown in step (a) to have a deficient plasma melatonin level as measured by a deficient level of 6-sulfatoxymelatonin in the urine; and (c) administering an effective plasma melatonin deficiency correcting amount of melatonin to the selected infant(s) from step (b); wherein the screening step (a) includes a method for the determination of 6-sulfatoxymelatonin as a component of interest in the urine, in accordance with the method of the invention set forth herein.

The melatonin administered in step (c) may be, but is not necessarily, in the form of a pharmaceutical controlled-release formulation. Such a slow-release formulation may be, but is not necessarily, such that melatonin is released therefrom in the body in simulation of the normal endogenous human melatonin plasma profile.

It will be appreciated that infants treated in accordance with the invention can be monitored in order to determine when it is safe to discontinue such administration which thus simulates the normal melatonin plasma profile.

DETAILED DESCRIPTION OF THE INVENTION

Figure 1:
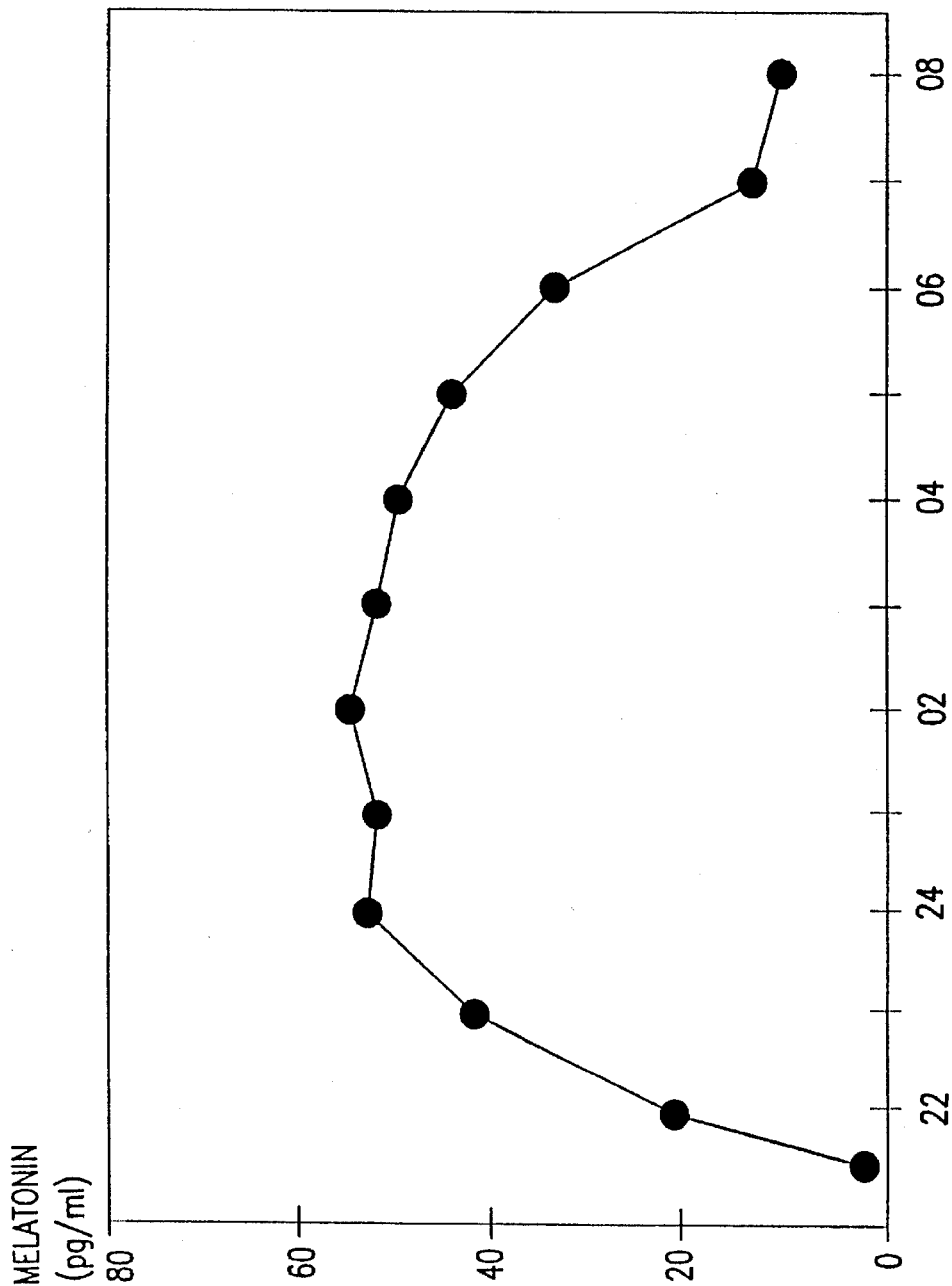
FIG. 1 is a graph illustrating the endogenous nocturnal profile of melatonin concentration in a healthy human.

The water-miscible organic solvent used in accordance with the present invention to extract the component(s) of interest from the used diapers includes by definition aqueous solutions of such water-miscible solvents. Thus, the term "solvents" includes inter alia materials which are solids at ordinary temperatures, where such solids are miscible with water. Included within the definition of water-miscible organic solvents for use in the method of the invention are the following:

water-miscible alcohols: e.g. methanol, ethanol, propanol, isopropanol, tertiary butanol;

water-miscible acids: e.g. formic acid, acetic acid, p-phenolsulfonic acid;

water-miscible bases: e.g. ethylamine, diethylamine, trimethylamine;

acetone;

acetonitrile;

dimethylsulfoxide;

water-miscible amides: e.g. dimethylformamide, pyrrolidone, N-methylpyrrolidone.

It will be appreciated that the above list is not exhaustive, and that the skilled person will be able to select one of these solvents or another water-miscible organic solvent e.g. according to the nature of the component(s) of interest or according to other relevant criteria known in the art.

As indicated above, the sequence of steps comprised in the method of the invention may be carried out only once, or any number of times on used diapers within a particular time period e.g. up to 24 hours, and, if desired (e.g. to assay metabolites released into the urine over a period) up to as many times as the diapers are changed in a given 24-hour period. In a particular embodiment, diapers used during a 10–24 hour period are retained and their time of replacement is noted.

The invention will be illustrated by the following non-limiting Examples.

EXAMPLE 1

(a) Introduction

As pointed out above, SIDS may be related to improper development of the pineal gland, which is a component of the circadian clock and produces melatonin. Abnormally low melatonin secretion can be positively identified by distorted rhythms in urinary excretion of the major melatonin metabolite, 6-sulfatoxymelatonin. Thus, we have assessed the development of circadian rhythms in 6-sulfatoxymelatonin excretion in a female infant as described below.

(b) Extraction of urine components

Diapers are collected during the course of one day, from a female infant at 4, 9 and 12 weeks after birth. The diapers are weighed, and the net water content of each one is calculated from the difference in weight between these used diapers and unused diapers of the same type and manufacture. The external diaper layer is removed, including insoluble materials (faeces) to leave wet diaper pulp, from which a sample (0.1–0.5 g) is collected and weighed. The sample is extracted with methanol or ethanol for four hours at room temperature, and the mixture is kept overnight at 4° C. The insoluble pulpy fibers are then removed by centrifugation (10,000 g/min), dried and weighed. Net pulpy water content is calculated by difference.

c) Determination of 6-sulfatoxymelatonin in urine

Aliquots of the extracts obtained in part (b), above, are diluted and assayed using standard procedures. In this case, urinary 6-sulfatoxymelatonin was measured by a sensitive radioimmunoassay method using $^{125}$I-labelled 2-iodo-6-sulfatoxymelatonin (Stockgrand, U.K.).

(d) Assessment of extraction procedure efficiency

A 6-sulfatoxymelatonin solution was poured onto an unused diaper and then extracted as described above. Recovery of 6-sulfatoxymelatonin from the diaper was more than 95%

(e) Assessment of extraction procedure reproducibility

Samples were collected from various areas of the infant's wet diapers, and 6-sulfatoxymelatonin was extracted and assayed as described above.

The results of the assays described in parts (c) and (e), above, are shown respectively in Tables I and II below.

TABLE I

Amount (μg/diaper) of urinary 6-sulfatoxymelatonin excreted at time intervals by a female infant.

| Time | Age (weeks) | | |
|---|---|---|---|
| | 4 | 9 | 12 |
| 08:00 | 0.14 | 0.63 | 4.6 |
| 12:30 | 0.13 | 1.8 | — |
| 12:45 | 0.32 | 2.5 | — |
| 16:00 | — | 2.5 | 13 |
| 17:45 | — | 2.2 | 9.3 |
| 20:30 | 0.58 | — | 10.5 |
| 20:50 | — | 3.2 | 17 |
| 22:30 | 0.108 | — | 13 |
| Total daily excretion | 1.278 | 9.076 | 67.4 |

Note on Table I: the total daily excretion figures at 4 and 9 weeks agree with the approximate daily excretion amounts shown for similar ages in FIG. 3 of Rager et al ("6-Hydroxymelatonin sulfate excretion in children from newborn age to adulthood" in Advances in Pineal Research, Reiter R. J. and Pang S. F. Eds., John Libbey & Co. Ltd., 1989, at pp. 299–304). Rager et al do not show any data with which the 12 week 24-hour excretion figure of 67.4 can be compared directly, but it lies within the broad range shown for older children up to 10 years old (Rager et al, FIG. 1). It appears, therefore, that the results shown in Table I are those of an infant whose pineal gland is developing normally with respect to excretion of melatonin.

TABLE II

Amount (μg/diaper) of urinary 6-sulfatoxymelatonin in samples from various loci of the same diaper

| Diaper No. | Sample No. | | | | X ± SD |
|---|---|---|---|---|---|
| | 1 | 2 | 3 | 4 | |
| 1 | 22.9 | 16.7 | 16.9 | — | 18.8 ± 3.5 |
| 2 | 11.6 | 15.4 | 8.6 | 11.2 | 11.7 ± 2.8 |
| 3 | 6.2 | 8.2 | 5.1 | 4.5 | 6.1 ± 1.49 |

In Example 1, above, there has been described inter alia the extraction of urine components, in particular 6-sulfatoxymelatonin, from diapers and quantitative determination of 6-sulfatoxymelatonin. However, as will be appreciated by skilled persons, the present invention is not limited to the determination of 6-sulfatoxymelatonin, but may also be applied to the determination of other urinary components. It will further be appreciated by skilled persons that even where the determination of 6-sulfatoxymelatonin is concerned, this may be done by any appropriate method known in the art and is not restricted to a radioimmunoassay.

EXAMPLE 2

The general procedure described in parts (b) and (c) of Example 1 was carried out on a 15 month-old male infant, with the detailed results shown in Table III.

TABLE III

Determination of amount of urinary 6-sulfatoxymelatonin excreted at time intervals by a 15-month male infant

| Time | Diaper wt. (g) | | Sample wt. (g) | | | 6-sulfatoxymelatonin | |
|---|---|---|---|---|---|---|---|
| | gross | net | wet | dry | net | ng/ml | μg/diaper |
| 22:00 (day 1) | 169 | 129 | 0.206 | 0.011 | 0.195 | 2.7 | 1.8 |
| day 2: | | | | | | | |
| 08:30 | 244 | 204 | 0.265 | 0.013 | 0.252 | 28.0 | 22.7 |
| 12:00 | 330 | 290 | 0.278 | 0.013 | 0.265 | 9.1 | 10.0 |
| 16:00 | 297 | 257 | 0.245 | 0.010 | 0.235 | 3.5 | 3.8 |
| 22:00 | 266 | 226 | 0.230 | 0.010 | 0.220 | 4.5 | 4.6 |
| Total daily excretion | | | | | | | 41.1 |

Note on Table III: the total daily excretion figure of 41.1 shows good agreement with the mean daily excretion amount for 1–6 years old depicted in FIG. 2 of Rager et al (loc cit).

EXAMPLE 3

Introduction

If a urinary assay such as has been described in Examples 1 and 2, above, reveals a deficiency in a component, e.g. a hormone, which should be present at a particular level in the subject's body, a physician of average competence would be able to prescribe medication in a particular dosage and form of administration, to counteract such deficiency and to raise the component in question to the required level.

Thus, where by way of example determination of 6-sulfatoxymelatonin in the urine has revealed a melatonin deficiency in the subject, a physician of average competence would be able to prescribe melatonin in a particular dosage and form of administration, to counteract such deficiency and to raise the level of melatonin to the required level. Where the subject is an infant, a physician or pediatrician would prescribe accordingly. Thus, the practitioner of average skill could select a suitable form of administration, e.g. from those described in the incorporated-by-reference documents mentioned above, or in particular could use a slow release formulation such as described in the present Example, from which melatonin is released in the body in simulation of the normal endogenous human melatonin plasma profile.

It is presently contemplated that a daily dosage rate for infants, whether to counteract a discovered deficiency or to prevent a deficiency occurring, i.e. for prophylactic use, could fall within the range of 1 μg to 1 mg melatonin, either as a pharmaceutical formulation or include in a conventional solid or liquid infant food (including a food supplement). The present invention accordingly includes such an infant food, which, apart from the incorporation of melatonin in accordance with the present invention, would be manufactured according to procedures known to persons in the art.

Preparation and Release Profile of Formulations (a) There were compressed in a 7 mm cylindrical punch at 2.5 tons, after dry mixing of the powdered materials, namely 1 mg/tablet melatonin (Biosynth Co., Switzerland) and acrylic resin carrier (Rohm Pharma), which was Eudragit RS100 (formulation SR-Ms) or Eudragit RSPO (formulation SR-Mf), besides other components as noted:

formulation SR-Ms: Eudragit RS100 48.8%, lactose 50%, melatonin 1.2%;

formulation SR-Mf: Eudragit RSPO 35.3%, lactose 16.7%, calcium hydrogen phosphate 41.4%, talc 1.3%, magnesium stearate 4% melatonin 1.3%.

A conventional dosage form (RM) was prepared similarly to formulation SR-Mf, but using lactose in place of Eudragit as carrier.

(b) The potential release profile of the tablets prepared as described in paragraph (a), was first investigated by in vitro dissolution of melatonin therefrom in distilled water at 37° C. The results in Table A show the % of the melatonin content (mean value of 6 tablets) which has dissolved at the stated intervals of time.

TABLE A

| melatonin (%) released from: | Time (hours) | | | | | |
|---|---|---|---|---|---|---|
| | 1 | 2 | 4 | 6 | 8 | 10 |
| SR-Ms | 12 | 29 | 62 | 84 | 90 | 100 |
| SR-Mf | 32 | 51 | 76 | 88 | 100 | |
| RM | 93 | 96 | 100 | | | |

(c) The in vivo profile of the SR-Mf tablets prepared as described in paragraph (a), was investigated by oral administration twice to a healthy male (age 36) at 10 a.m., i.e. when circulating melatonin levels are undetectable. The amount of melatonin released in vivo was determined by radioimmunoassay of its major metabolite, 6-sulfatoxymelatonin, in the urine. The amount of urinary 6-sulfatoxymelatonin closely reflects the blood level of the hormone. The results in Table B show the melatonin determined as a % of the total melatonin administered (mean value of 2 tablets).

TABLE B

| | In vivo release of melatonin from SR-Mf | | | | | |
|---|---|---|---|---|---|---|
| Time (hours) | 1 | 2 | 4 | 6 | 8 | 10 |
| % release at intervals | 10.7 | 25.7 | 40.6 | 14.0 | 7.0 | 1.9 |
| cumulative release % | 10.7 | 36.4 | 77.0 | 91.0 | 98.0 | 99.9 |

(d) The data in Table B show that it is possible to make a pharmaceutical formulation which simulates the release of melatonin in the human body according to the normal human endogenous melatonin plasma profile. It is noted that the release of melatonin in vitro, illustrated in Table A, provides only an approximate indication of the in vivo release profile due to the known phenomenon of the active compound being absorbed by the tissues in the early stages of release.

While particular embodiments of the invention have been particularly described hereinabove, it will be appreciated that the present invention is not limited thereto, since, as will be readily apparent to skilled persons, many variations and modifications can be made. Such variations and modifications which have not been detailed herein are deemed to be the obvious equivalents of the present invention. For example, analogs of melatonin which substantially imitate the function of melatonin in the human body are deemed to be obvious chemical equivalents of melatonin. To take another instance, whereas the present method for assaying components of interest which is particularly described herein includes weighing used and unused diaper, and weighing a used diaper sample before and after extraction of such components, the skilled addressee will be aware that in the alternative, since creatinine (by way of example) is believed to be excreted in an approximately constant amount of 25 mg/kg of body weight per day, determination of the ratio of the component(s) of interest to creatinine could avoid the necessity for such weighings. This type of alternative, using such a ratio, is deemed to be an obvious equivalent of the method of the invention. The essential concept, spirit and scope of the present invention will be better understood in the light of the claims which follow.

We claim:

1. A method for the determination of non-volatile organic components of interest in the urine of human subjects using diapers, which comprises carrying out the following sequence of steps at least once and up to as many times as the diapers are changed in a given 24-hour period, namely: providing a diaper which has been used to absorb urine from a human subject, removing the outer cover and any extraneous material so as to leave substantially only diaper pulp having urine absorbed thereon, estimating the amount of water in said used diaper, extracting a weighed portion of the diaper pulp having urine absorbed thereon with a water-miscible organic solvent, in which the diaper pulp is insoluble, to give an extract containing a component of interest, and determining the amount of the component of interest per unit volume of urine which was absorbed on the diaper pulp by assaying an aliquot of said extract.

2. A method according to claim 1, wherein said water-miscible organic solvent comprises at least one member selected from water-miscible alcohols, water-miscible acids, water-miscible bases, acetone, acetonitrile, dimethylsulfoxide and water-miscible amides.

3. A method according to claim 2, wherein said water-miscible organic solvent comprises at least one member selected from methanol and ethanol.

4. A method according to claim 1, wherein said component of interest is selected from hormones and metabolites.

5. A method according to claim 4, wherein said component of interest is selected from corticosteroids, creatinine, uric acid and catecholamines.

6. A method according to claim 4, wherein said component of interest is 6-sulfatoxymelatonin.

7. A method for the determination of 6-sulfatoxymelatonin in the urine of human subjects using diapers, which comprises carrying out the following sequence of steps at least once and up to as many times as the diapers are changed in a given 24-hour period, namely: providing a diaper which has been used to absorb urine from a human subject, removing the outer cover and any extraneous material so as to leave substantially only diaper pulp having urine absorbed thereon, estimating the amount of water in said used diaper, extracting a weighed portion of the diaper pulp having urine absorbed thereon with a water-miscible organic solvent, in which the diaper pulp is insoluble, to give an extract containing 6-sulfatoxymelatonin, and determining the amount of 6-sulfatoxymelatonin per unit volume of urine which was absorbed on the diaper pulp by assaying an aliquot of said extract, and wherein said water-miscible organic solvent comprises at least one member selected from water-miscible alcohols, water-miscible acids, water-miscible bases, acetone, acetonitrile, dimethylsulfoxide and water-miscible amides.

8. A method according to claim 7, wherein said water-miscible organic solvent comprises at least one member selected from methanol and ethanol.

9. An infant food for use in preventing or counteracting a melatonin deficiency in infants, which includes an amount of melatonin based on an amount of such food suitable for ingestion in a 24-hour period, within the range of 1 µg to 1 mg melatonin.

10. A method for treating an infant susceptible to sudden infant death syndrome (SIDS) which comprises:
 (a) screening infants to determine each infant's endogenous plasma melatonin level by measuring the amount of 6-sulfatoxymelatonin in the child's urine;
 (b) selecting at least one infant shown to have a deficient endogenous plasma melatonin level; and
 (c) administering to each of said infants melatonin in amounts sufficient to correct the plasma melatonin deficiency.

11. A method in accordance with claim 10, wherein the melatonin is administered in an amount and in a form such that the infant's plasma melatonin profile simulates a normal infant's endogenous melatonin profile.

12. A method in accordance with claim 10, wherein the amount of 6-sulfatoxymelatonin in the infant's urine is determined by:
 (a) providing a diaper which has absorbed urine from said infant,
 (b) isolating the urine-containing pulp of the diaper from other components of the diaper.
 (c) estimating the amount of water in said diaper,
 (d) extracting a weighed portion of the diaper pulp having urine absorbed thereon with a water-miscible organic solvent in which the diaper pulp is insoluble to give an extract comprising 6-sulfatoxymelatonin, and
 (e) determining the amount of 6-sulfatoxymelatonin per unit volume of urine absorbed on the diaper pulp.

13. A method in accordance with claim 12, wherein said water-miscible organic solvent comprises at least one member selected from water-miscible alcohols, water-miscible acids, water-miscible bases, acetone, acetonitrile, dimethylsulfoxide and water-miscible amides.

14. A method in accordance with claim 13, wherein said water-miscible alcohol comprises methanol or ethanol.

15. A method in accordance with claim 10, wherein the 6-sulfatoxymelatonin is measured over a 24 hour period.

16. A method in accordance with claim 10, wherein the melatonin to be administered is mixed with an infant food or a pharmaceutical formulation.

17. A method in accordance with claim 10, wherein the melatonin is administered in the form of a pharmaceutical controlled-release formulation.

18. A method of treating an infant susceptible to SIDS which comprises
 (a) screening infants to determine each infant's endogenous plasma melatonin level as measured by the profile of 6-sulfatoxymelatonin in the urine over a 24-hour period;
 (b) selecting at least one infant shown to have a deficient endogenous plasma melatonin profile; and
 (c) administering to each of said selected infants melatonin in amounts sufficient to correct the plasma melatonin deficiency.

* * * * *